United States Patent [19]

Kremer et al.

[11] 4,341,899

[45] Jul. 27, 1982

[54] VAPOR PHASE DECHLORINATION PROCESS

[75] Inventors: Ross A. Kremer, Belle Mead; Leopoldo C. Mansueto, Jr., Gillette, both of N.J.

[73] Assignee: Rhone-Poulenc Agrochimie, Lyons, France

[21] Appl. No.: 118,174

[22] Filed: Feb. 4, 1980

[51] Int. Cl.³ .............................................. C07C 69/78
[52] U.S. Cl. ...................................... 560/103; 560/21
[58] Field of Search ......................................... 560/103

[56] References Cited

PUBLICATIONS

Elles, *Hydrogenation of Organic Substances*, D. Van Nostrand Co., Inc., N.Y., 3rd Edition, p. 113, (1930).

Rose, *The Condensed Chemical Dictionary*, 5th Ed., Reinhold Publishing Co., N.Y., p. 357, (1956).

Weygand, *Preparative Organic Chemistry*, pp. 65–66, (1972).

*Primary Examiner*—G. T. Breitenstein
*Attorney, Agent, or Firm*—Morgan, Finnegan, Pine, Foley & Lee

[57] ABSTRACT

This invention provides a selective dechlorination process that comprises contacting a vaporized mixture of methyl 2,5-dichlorobenzoate and hydrogen, in a molar ratio respectively of 1:3–4, optionally together with between about 1% and about 10% of methanol by weight of methyl 2,5-dichlorobenzoate with a nickel catalyst at a temperature between about 200° C. and about 300° C. and for a residence time of between about 2.0 seconds and about 5.0 seconds.

3 Claims, No Drawings

VAPOR PHASE DECHLORINATION PROCESS

BACKGROUND OF THE INVENTION

1. Field of the Invention

This invention is directed to a process for selective dechlorination of methyl 2,5-dichlorobenzoate.

2. Description of the Prior Art

Insofar as is now known, the process of this invention has not been proposed.

SUMMARY OF THE INVENTION

This invention provides a selective dechlorination process that comprises contacting a vaporized mixture of methyl 2,5-dichlorobenzoate and hydrogen, in a molar ratio respectively of 1:3–4, optionally together with between about 1% and about 10% of methanol by weight of methyl 2,5-dichlorobenzoate with a nickel catalyst at a temperature between about 200° C. and about 300° C. and for a residence time of between about 2.0 seconds and about 5.0 seconds.

DESCRIPTION OF SPECIFIC EMBODIMENTS

In the commercial process for producing herbicidal bifenox, i.e., methyl 2-nitro-5-(2'4'-dichlorophenoxy)-benzoate, preparation of a reaction precursor involves the chlorination of benzoyl chloride to obtain m-chlorobenzoyl chloride. This material is then reacted with methanol to produce the corresponding methyl chlorobenzoate.

In practice, however, there is obtained a mixture of desired methyl m-chlorobenzoate and undesired methyl 2,5-dichlorobenzoate. Because of the difference in boiling points, these compounds are easily separated. The object of this invention is to provide a method for dechlorinating selectively the methyl 2,5-dichlorobenzoate to desired methyl m-chlorobenzoate to obtain more of the useful precursor.

This is accomplished by contacting, in the vapor phase, a mixture of methyl 2,5-dichlorobenzoate, hydrogen, and, optionally, methanol with a nickel catalyst. The molar ratio of methyl 2,5-dichlorobenzoate:hydrogen is between about 1:3 and about 1:4. The amount of methanol in the feed, if used, is between 1% and about 10% by weight based upon the weight of methyl 2,5-dichlorobenzoate.

As has been indicated hereinbefore, the use of methanol co-feed is optional, but it is preferred practice. The use of methanol permits longer catalyst life and better selectivity, particularly at higher temperatures.

Although the feed mixture can be vaporized in the reactor, in practice it is more feasible to vaporize the feed and feed it continuously to the reactor in vapor phase. The reactor temperature will be between about 200° C. and about 300° C. The feed will be fed at a rate to maintain a residence time in the reactor of between about 2.0 seconds and about 5.0 seconds. As is usual in continuous processes, unreacted methyl 2,5-dichlorobenzoate can be recycled to extinction.

The catalyst used in the process of this invention is metallic nickel, which can be supported or unsupported. A preferred catalyst contains 40–60% nickel on kieselguhr.

EXAMPLE 1

Into a vapor phase reactor was charged 24 g. of a 52% nickel-on-kieselguhr catalyst and the reactor was heated to reaction temperature (230° C.) in the presence of hydrogen. When reaction temperature was reached, a reactant mixture of methyl 2,5-dichlorobenzoate (DCBE) and hydrogen was continuously vaporized and fed to the reactor in a molar ratio of 1:3.7 DCBE:$H_2$. The reactants were fed at a rate such that the reactor residence time was 3.2 seconds until 360 g. DCBE had been fed (15 wts./wt. catalyst). Product from the reactor was continuously condensed and collected. Analysis by gas chromatography showed a DCBE conversion of 33% with a selectivity to methyl m-chlorobenzoate (CBE) of 70%.

EXAMPLE 2

Example 1 was repeated except that the reaction temperature was 260° C. and 720 g. DCBE were fed to the reactor (30 wts./wt. catalyst). Analysis showed a DCBE conversion of 40% and a selectivity to CBE of 54%.

The beneficial effect of methanol on the process was determined by carrying out the following two experiments.

EXAMPLE 3

Example 1 was repeated except that 3 wt.% methanol (based on DCBE) was co-fed to the reactor (230° C.) with the DCBE and hydrogen until 792 g. of DCBE had been fed (33 wts. DCBE/wt. catalyst). Product analysis showed a DCBE conversion of 33% and a selectivity to CBE of 75%.

EXAMPLE 4

Example 3 was repeated except that the reaction temperature was raised to 260° C. and DCBE was fed until 840 g. were fed to the reactor (35 wts. DCBE/wt. catalyst). Product analysis showed a DCBE conversion of 40% and a selectivity to CBE of 71%.

The data from Examples 1–4 are summarized in the following Table.

TABLE

VAPOR PHASE CATALYTIC DECHLORINATION OF METHYL 2,5-DICHLOROBENZOATE (DCBE) TO METHYL m-CHLOROBENZOATE (CBE) OVER 52% NICKEL-ON-KIESELGUHR CATALYST

| Reaction Temperature- °C. | Mole Ratio $H_2$: DCBE In Feed | Methanol In Feed - Wt. % Based On DCBE | Reactor Residence Time - Sec. | Total Wt. DCBE Fed - g. | DCBE Conversion-% | Selectivity To CBE - % |
|---|---|---|---|---|---|---|
| 230 | 3.7:1 | 0 | 3.2 | 360 | 33 | 70 |
| 260 | 3.7:1 | 0 | 3.2 | 720 | 40 | 54 |
| 230 | 3.7:1 | 3.0 | 3.2 | 792 | 33 | 75 |
| 260 | 3.7:1 | 3.0 | 3.2 | 840 | 40 | 71 |

Catalyst Weight in all Runs was 24.0 g.

The methyl m-chlorobenzoate product of the process of this invention is nitrated by known methods to produce methyl 2-nitro-5-chlorobenzoate. The latter compound is then reacted with the potassium salt of 2,4- dichlorophenol in the Ullmann ether synthesis to produce bifenox. Bifenox is a known commercial herbicide.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A selective dechlorination process that consists essentially of contacting a vaporized mixture of methyl 2,5-dichlorobenzoate and hydrogen, in a molar ratio respectively of 1:3-4, together with between about 1% and about 10% of methanol by weight of methyl 2,5-dichlorobenzoate with a nickel catalyst at a temperature between about 200° C. and about 300° C. and for a residence time of between about 2.0 seconds and about 5.0 seconds.

2. The process of claim 1, wherein methanol is co-fed with the feed mixture.

3. The process of claims 1 or 2, wherein said catalyst is 40–60% nickel on kieselguhr.

* * * * *